United States Patent
Yap et al.

(10) Patent No.: US 6,796,977 B2
(45) Date of Patent: Sep. 28, 2004

(54) VARIABLE GRAFT TENSIONER

(75) Inventors: Marc C. Yap, Millville, UT (US); Daniel F. Justin, Logan, UT (US); David A. McGuire, Anchorage, AK (US)

(73) Assignee: DePuy Mitek, Inc., Norwood, MA (US)

( * ) Notice: Subject to any disclaimer, the term of this patent is extended or adjusted under 35 U.S.C. 154(b) by 148 days.

(21) Appl. No.: 09/967,317

(22) Filed: Sep. 28, 2001

(65) Prior Publication Data

US 2003/0065247 A1 Apr. 3, 2003

(51) Int. Cl.[7] .............................................. A61B 19/00
(52) U.S. Cl. .............................. 606/1; 600/36; 606/53; 606/88; 623/13.11
(58) Field of Search ............... 600/36; 623/13.11–13.14; 69/19.3; 606/1, 53, 63, 86, 87, 88, 89, 90, 99, 102, 151; 269/55, 65, 86

(56) References Cited

U.S. PATENT DOCUMENTS

| | | | | |
|---|---|---|---|---|
| 4,649,916 A | * | 3/1987 | Frimberger | ..................... 606/1 |
| 5,298,012 A | * | 3/1994 | Handlos | ..................... 600/36 |
| 5,397,357 A | * | 3/1995 | Schmieding et al. | ......... 606/86 |
| 5,415,651 A | | 5/1995 | Schmieding | |
| 5,562,668 A | | 10/1996 | Johnson | |
| 5,570,706 A | * | 11/1996 | Howell | ....................... 128/898 |
| 5,571,184 A | | 11/1996 | DeSatnick | |
| 5,632,748 A | | 5/1997 | Beck, Jr. et al. | |
| 5,683,400 A | * | 11/1997 | McGuire | ..................... 606/96 |
| 5,713,897 A | | 2/1998 | Goble et al. | |
| 5,928,264 A | * | 7/1999 | Sugarbaker et al. | ........ 606/207 |
| 6,001,106 A | | 12/1999 | Ryan et al. | |
| 6,106,556 A | | 8/2000 | Demopulos et al. | |
| 6,152,928 A | | 11/2000 | Wenstrom, Jr. | |
| 6,278,079 B1 | * | 8/2001 | McIntyre et al. | ...... 219/121.67 |

FOREIGN PATENT DOCUMENTS

| | | |
|---|---|---|
| DE | 41 12 205 A1 | 10/1992 |
| DE | 198 14 564 C1 | 1/2000 |
| FR | 2 814 359 A1 | 3/2002 |

* cited by examiner

Primary Examiner—Michael Peffley
(74) Attorney, Agent, or Firm—Nutter McClennen & Fish LLP

(57) ABSTRACT

A graft preparation board that enables an exact tensioning of soft tissue grafts. The graft preparation board allows the amount of tensile load to be easily determined so that the operator can precisely control the amount of tension to be applied. The graft preparation board also enables higher tensions to be placed on graft tissues to be used in surgery.

13 Claims, 3 Drawing Sheets

VARIABLE GRAFT TENSIONER

CROSS-REFERENCE TO RELATED APPLICATIONS

Not applicable.

STATEMENT REGARDING FEDERALLY SPONSORED RESEARCH

Not applicable.

FIELD OF THE INVENTION

The present invention relates to a device and method for preparing graft tissue for tissue replacement surgery. More specifically, the invention relates to a preparation board for tensioning graft tissue prior to implantation at an injury site.

BACKGROUND

The complete or partial detachment of ligaments, tendons or other soft tissues from their associated bones within the body are relatively commonplace injuries, particularly among athletes. Such injuries are generally the result of excess stress being placed on these tissues. Tissue detachment may occur as the result of an accident such as a fall, overexertion during a work related activity, during the course of an athletic event or in any one of many other situations and/or activities. In the case of a partial detachment, commonly referred to under the general term "sprain", the injury will frequently heal itself, if given sufficient time, and if care is taken not to expose the injury to any undue stress during the healing process. If, however, the ligament or tendon is completely detached from its associated bone or bones, or if it is severed as part of a traumatic injury, partial or permanent disability may result. Fortunately, a number of surgical techniques exist for reattaching such detached tissues and/or completely replacing severely damaged tissues.

A typical surgical correction of a tendon or ligament injury involves the fixed attachment of the tendon or ligament substitute (often formed of autogenous tissue harvested from elsewhere in the body) to the area of normal bony attachment so that regrowth and reattachment of the tendon or ligament substitute to the bone is enabled. Attachment of the ligament substitute to the bone is ensured by the use of bone attachment means using "traditional" attachment devices such as metal staples, sutures over buttons and cancellous bone screws. Such "traditional" attachment devices have also been used to attach tendon or ligament substitutes to the desired bone or bones. The ligament substitute to bone attachment means must be rigidly situated so that regrowth of the ligament substitute in the bony area of the attachment point is undisturbed.

A common type of injury to the knee is the tearing of the anterior cruciate ligament (ACL). Located in the center of the knee joint and running from the femur (thigh bone) to the tibia (shin bone), through the center of the knee, the ACL is the major stabilizing ligament of the knee. Surgical treatment of a torn anterior cruciate ligament usually involves an arthroscopic surgical reconstruction of the injured ligament. A number of different types of tissues can be utilized to reconstruct the ACL, the most common of which involves harvesting the central third of the patellar tendon with a bone block at each end of the tendon graft. After harvesting the tissue, drill guides are used to place holes into the tibia and femur. By placing the drill holes at the attachment sites of the original ligament, when the graft is pulled through the drill hole and into the knee, it will be placed in the same position as the original ACL. After pulling the graft through the drill holes and into the joint to replace the torn ACL, the graft is then held in place with bioabsorbable screws or metallic screws. New blood vessels are allowed to grow into the graft and the site is allowed to heal.

While the patellar tendon is the most widely used autograft tissue, surgical morbidity associated with its harvest has led to an increase in the use of alternate grafts. Currently proposed alternatives include double stranded hamstring tendons and other soft tissue grafts for creating composite grafts. An exemplary technique for using double stranded hamstring tendons requires pretensioning the tendons on a graft preparation board until they are ready for use. This pretensioning process involves holding the graft tissue across the board and applying a tensile load to the tissue. Before the composite graft is implanted, the tendons can be whip stitched at their ends while under tension to create a secure bundle and prevent fraying.

Once the tendon graft is prepared, the tendons may be doubled over, and then inserted, doubled end first, through a drilled tibial tunnel. Attachment means, such as the ligament fixation device disclosed by Wenstrom, Jr. in U.S. Pat. No. 6,152,928, may be used to secure the doubled end to the opening of the femoral socket. Sutures from the whip stitched ends provide a means by which the composite graft can be connected to an in situ tensioner and the composite graft tensioned and the knee ranged approximately 12 to 14 times from extension to flexion. While maintaining tension and spreading apart the individual strands of the composite graft, the soft tissue graft can be fixed to the anterior tibia. Fixation may be achieved by inserting an expandable sheath up the tibial tunnel, into the opening resulting from the spreading and tensioning of the strands. Fixation may be achieved, for example, by screwing an expander screw into the sheath to engage the sheath with the strands and tibia.

Regardless of whether a patellar tendon or a double stranded hamstring tendon is used, one important factor in ensuring the success of the ACL surgery is the adequacy of tensioning of the graft tissue during its preparation. Current graft preparation boards for pretensioning harvested graft tissue, such as the one disclosed by Schmieding in U.S. Pat. No. 5,415,651, comprise a pair of rudimentary holding blocks that are linearly displaceable along a track. Each end of the graft tissue is secured to a block. Each block is held in position in one of a plurality of predetermined holes along the track by a vertical pin. To effect tensioning of the graft, the pins are released and the blocks moved apart by a fixed length along the track. When the pin or pins align with one of the holes along the track, the blocks are resecured.

Though such a preparation board may provide adequate tensioning of the graft tissue for some types of graft preparations, there is no means to precisely control the amount of tension to be applied. Further, the boards currently available do not allow the user to measure with accuracy the amount of tension being applied. There is thus a need for a graft preparation board that enables the operator to easily to control and monitor the amount of tension to be applied to the graft tissue. There is also a need for a graft tensioner that is able to place higher tensions than normally possible by simply pulling axially on one end of a soft tissue graft.

SUMMARY OF THE INVENTION

The present invention avoids the aforementioned problems associated with current graft tension boards by providing a graft preparation board that enables an exact tensioning of soft tissue grafts. In the present invention, the amount of tensile load can be easily determined so that the operator can precisely control the amount of tension to be applied. The present graft preparation board also enables higher tensions to be placed on the tissues to be used in surgery.

In one embodiment of the present invention, the graft preparation board has a platform on which there is a first unit and a second unit. On the second unit is a second grasping element for securing an opposite end of the tissue graft. The first unit includes a tensioning device which comprises a base member and a translating element that extends through the base member. The translating element is connected at one end to a head that extends into a first grasping element for securing an end of a tissue graft. Translating element is connected at an opposite end to a grip. Extending between the grip and base member is a spring mechanism. By deploying the grip, the spring mechanism can be tensioned as the translating element is moved, effecting a linear displacement of the translating element with respect to the head and base member. In this particular embodiment, the translating element can comprise a sliding threaded shaft, and the grip can comprise a knob such that, when the knob is turned, the sliding threaded shaft translates with respect to the head and the base member when the spring mechanism is tensioned.

In another embodiment of the present invention, the translating element can include a sliding shaft having notches or grooves instead of threads that would enable the shaft to incrementally ratchet to allow the first grasping element any number of predetermined distances with respect to base member. It is envisioned that the tensioning device of the present invention could work as well with a pulley or reel system for the translating system.

In one aspect of the present invention, the first and second units may be translatable along the length of the platform. For instance, first and second units can be slidable along a track that extends on the platform. Each unit can be locked in position on the track. The board may include indicia along the side of the platform for determining the length of the graft tissue held between the first and second grasping elements.

In another aspect of the present invention, the first and second grasping elements can comprise jaws. However, first and second grasping element can also be hooks, pins, or posts for engaging an end of the graft tissue to be prepared.

In yet another aspect of the present invention, the base member can include a window having indicia representing units of tension (lbs. and N) surrounding the window. Within the window is an indicator for reading the amount of tensile load being applied to the graft tissue being held within the first and second grasping elements.

Further features of the invention, its nature and various advantages, will be more apparent from the accompanying drawings and the following detailed description of the drawings and the preferred embodiments.

DETAILED DESCRIPTION OF THE INVENTION

Figure 1:
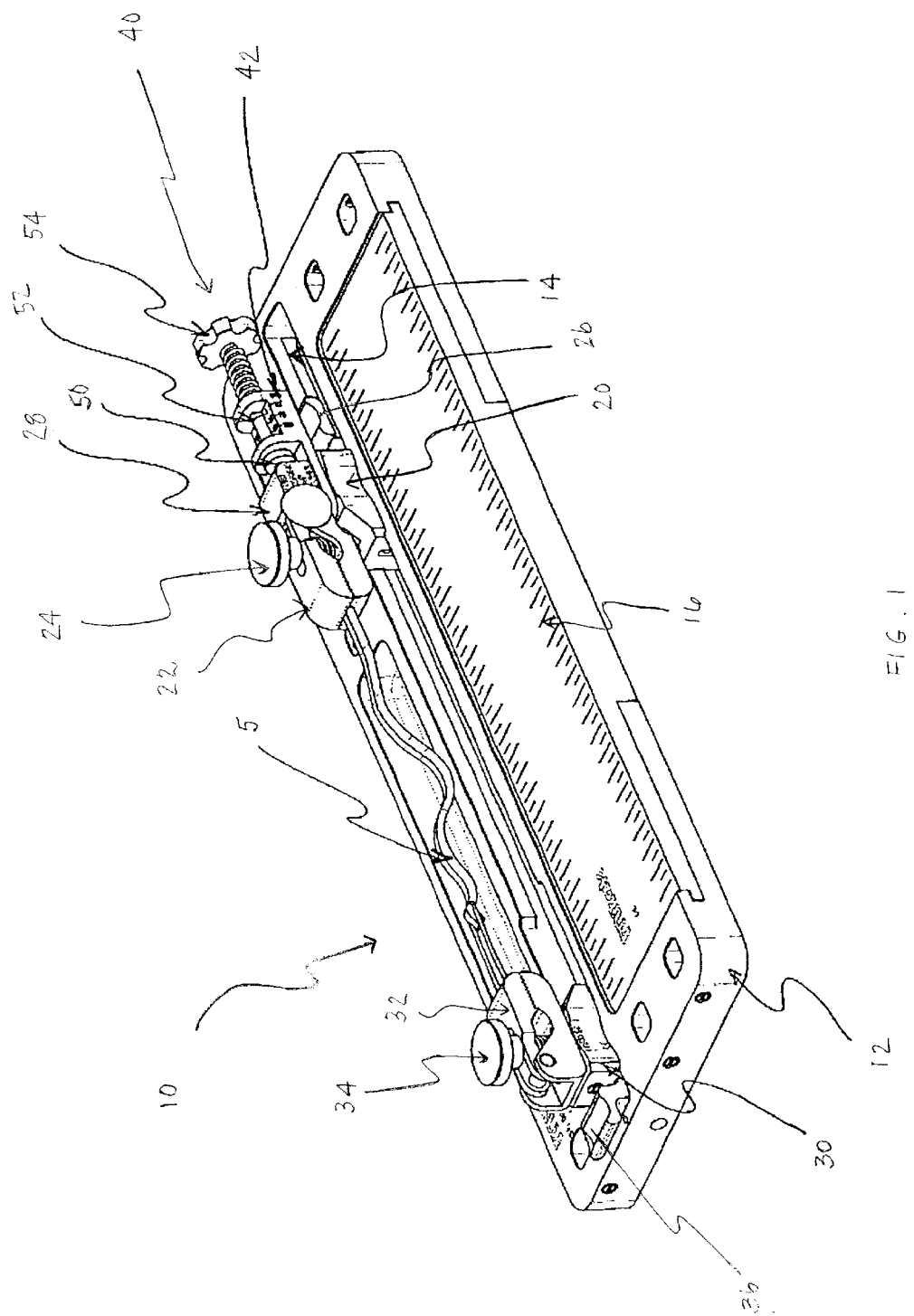
FIG. 1 is a perspective view of one embodiment of a graft preparation board of the present invention.

Referring now to FIG. 1, a graft preparation board 10 is shown having a platform 12 on which there sits a first unit 20 and second unit 30 for preparing and tensioning a graft tissue 5 prior to implantation. The first unit 20 can be translatable, or linearly displaceable with respect to the platform 12. As illustrated, first unit 20 is slidable along a track 14 that extends the length of the platform 12. On the first unit 20 is a first grasping element 22 for holding one end of graft tissue 5. As detailed in FIGS. 2 and 3, in this embodiment the first grasping element 22 comprises a pair of jaws that can be opened and locked shut by adjusting threaded nut 24 extending through the jaws. First unit 20 can also include a locking mechanism 26 for holding the first unit 20 stationary on the platform 12.

Also on platform 12 is a second unit 30 that includes a second grasping element 32 for holding an opposite end of graft tissue 5. Second grasping element 22 comprises a pair of jaws that are opened and locked with threaded nut 34. Second unit 30 can also be slidable along the track 14 of platform 12. By having either or both first 20 and second units 30 translatable, first unit 20 and/or second 30 unit can be moved to accommodate the particular length of the graft tissue 5 to be tensioned. This enables the units 20, 30 to hold the graft tissue 5 taut against the platform 12, regardless of length. Indicia 16 representing units of length (inches, cm, etc.) can be provided along the side of the platform 12 for reading the length of tissue 5.

Figure 2:
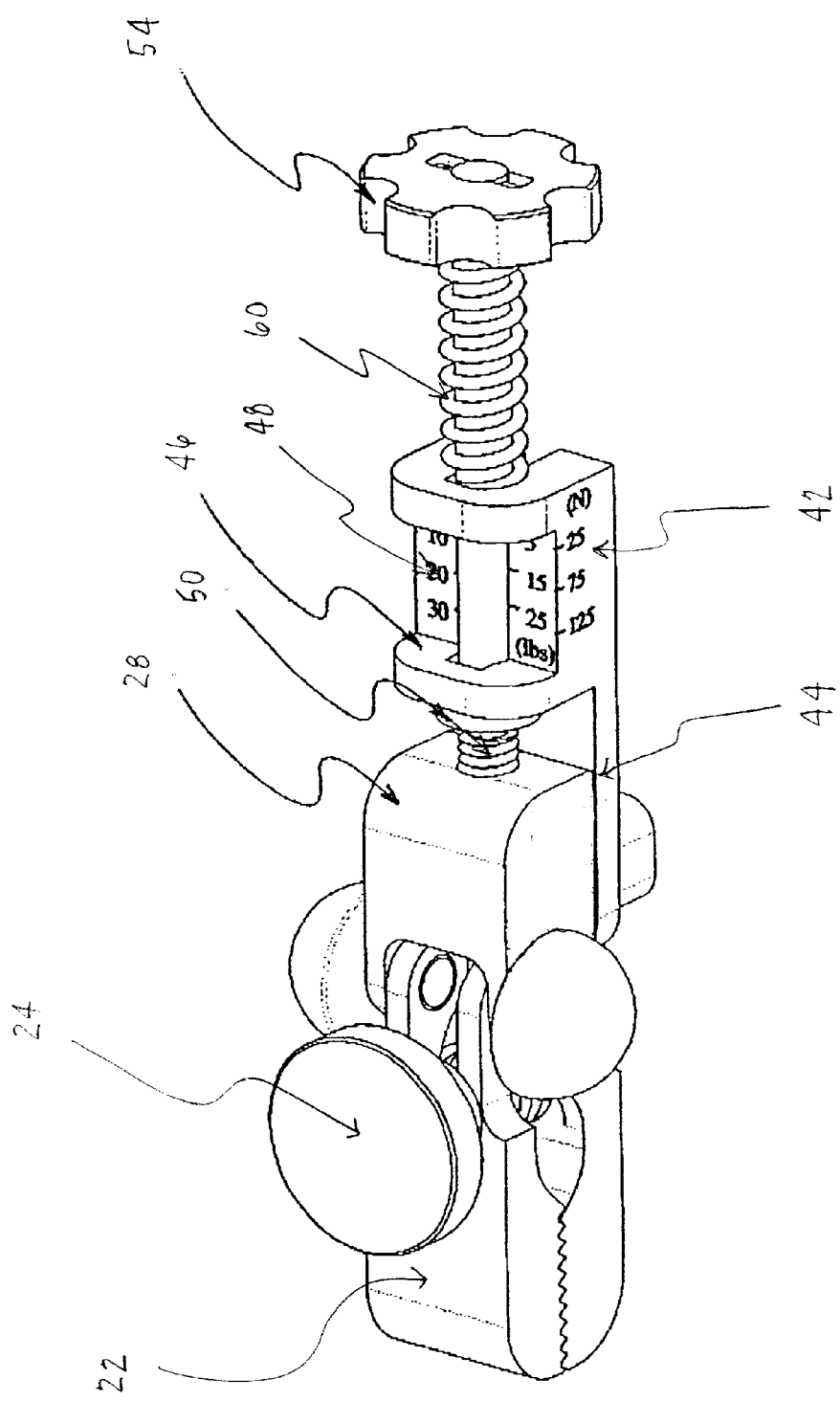
FIG. 2 is a detailed view of the tensioning device of FIG. 1.
Figure 3:
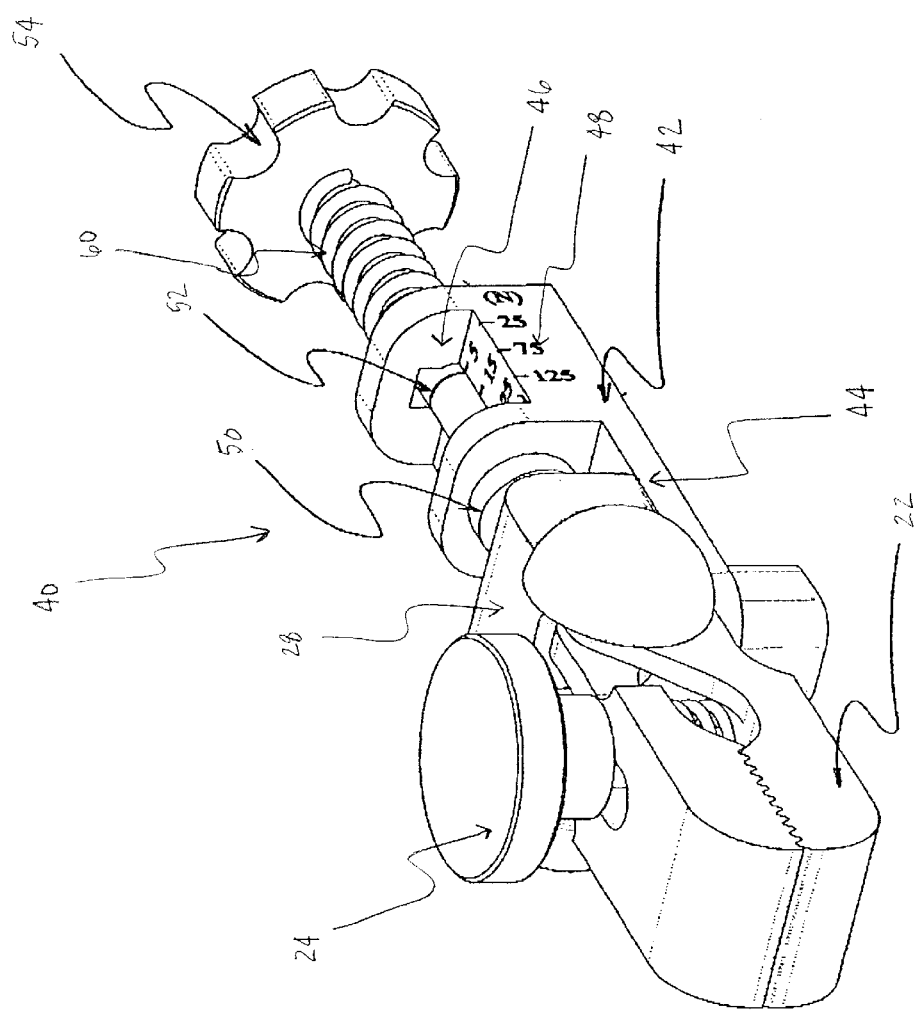
FIG. 3 is yet another perspective view of the tensioning device of FIG. 2.

Graft preparation board 10 also includes a tensioning device 40 on first unit 20. As shown in FIGS. 2 and 3, tensioning device 40 comprises a base member 42 and a translating element extending through the base member 42. The translating element enables the first grasping element 22 to be linearly displaced with respect to the first unit 20, which is connected to a flange 44 extending from base member 42. In this particular embodiment, the translating element comprises a sliding threaded shaft 50 that is attached at a distal-most end to a head 28 extending from first grasping element 22. At the proximal-most end of threaded shaft 50 is a grip such as a knob 54. Tensioning device 40 also includes a spring mechanism 60 on the sliding threaded shaft 50 between the knob 54 and base member 42.

In use, sliding threaded shaft 50 can translate with respect to both the head 28 and the base member 42 when tension is applied. If no tension exists, i.e., spring mechanism 60 is not compressed, when knob 54 is rotated, then the head 28 can translate with respect to the sliding threaded shaft 50 and base member 42. In this instance, the sliding threaded shaft 50 does not translate with respect to the base member 42. However, where an initial tension exists, i.e., the spring mechanism is compressed, then both the head 28 and the sliding threaded shaft 50 can translate with respect to each other, and with respect to the base member 42 when knob 54 is rotated.

First unit 20 and tensioning device 40 of graft preparation board 10 not only provide controlled induction of tensile load on the graft tissue 5, but can also measure the exact tensile load according to the translation of the sliding threaded shaft 50 relative to the base member 42, as calculated by the displacement of spring mechanism 60. As shown in FIG. 3, base member 42 includes a cut-away window 46 surrounding which are indicia 48 representing units of tensile load, e.g., lbs, N. Extending through window 46 is a portion of sliding threaded shaft 50 having thereon an indicator, or marking 52. Marking 52 can be a groove machined into the sliding threaded shaft 50, or just a superficial marking on the sliding threaded shaft 50.

To tension the graft tissue 5 held between first grasping element 22 and second grasping element 32, the knob 54 can be rotated so that spring mechanism 60 is displaced with respect to base member 42. In doing so, the first grasping element 22 is moved with respect to the distal-most end of the threaded shaft 50, thereby effectively stretching the graft tissue 5. That is, as tensile load is applied, the length of spring mechanism 60 becomes compressed as the tensile load pulls sliding threaded shaft 50 and first grasping element 22, and moving indicator 52 on sliding threaded shaft 50 further down and towards a distal-most end of window 46. The amount of compression, as measured by the spring's displacement, will be reflected in the position of the indicator or marking 52 on shaft 50 which, when lined up with indicia 48, can be read for determining the tensile load being placed on tissue graft 5.

While the first and second grasping elements 22, 32 are illustrated with jaws, it is contemplated that grasping elements can also comprise hooks, pins, or posts for engaging an end of the graft tissue 5 to be prepared. Though not shown, it is contemplated that the present invention can be used with graft tissue 5 having terminal bone blocks as well. Further, translating element may include a shaft having notches or grooves instead of threads that would enable shaft 50 to incrementally ratchet the first grasping element 22 any number of predetermined distances with respect to base member 42. It is envisioned that the tensioning device 40 of the present invention could work as well with a pulley or reel system for the translating system.

Graft tissue 5 to be prepared can be tensioned on the board 10 of the present invention until such time as the tissue 5 is ready for implantation. Before the composite graft is implanted, the tissue can be whip stitched at their ends to create a secure bundle and prevent fraying. Sutures from the whip stitched ends provide a means by which the composite graft can be connected to an in situ tensioner and the composite graft tensioned post implantation. This will provide adequate tensioning of the composite graft for optimal functioning at the implantation site.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A graft preparation board, comprising:
   a platform including a first unit having thereon a first grasping element for securing an end of a graft tissue, and a second unit having thereon a second grasping element for securing an opposite end of the graft tissue;
   the first grasping element being connected to the first unit by a tensioning device, the tensioning device comprising a base member and a translating element extending through the base member, the translating element being connected at one end to the first grasping element and at an opposite end to a grip;
   the tensioning device further including a spring mechanism on the translating element;
   wherein, when the spring mechanism is tensioned, deployment of the grip effects linear displacement of the translating element with respect to the first grasping element and base member.

2. The graft preparation board of claim 1, wherein the first unit is translatable along a length of the platform.

3. The graft preparation board of claim 2, wherein the second unit is translatable along the length of the platform.

4. The graft preparation board of claim 3, wherein the first and second units are slidable along a track extending on the platform.

5. The graft preparation board of claim 4, wherein each of the first and second units can be locked in position on the track.

6. The graft preparation board of claim 1, wherein the platform includes indicia along a length thereof, the indicia representing units of length.

7. The graft preparation board of claim 1, wherein the first and second grasping elements are selected from the group consisting of jaws, hooks, pins, and posts.

8. The graft preparation board of claim 1, wherein the base includes a window having indicia surrounding thereabout, the indicia representing units of tension.

9. The graft preparation board of claim 8, wherein the base further includes an indicator located within the window for reading the amount of displacement of the spring mechanism.

10. The graft preparation board of claim 1, wherein the translating element is a sliding threaded shaft.

11. The graft preparation board of claim 1, wherein the translating element is a notched shaft.

12. The graft preparation board of claim 1, wherein the grip is a knob.

13. A graft preparation board, comprising:
    a platform including a first unit having thereon a first grasping element for securing an end of a graft tissue, and a second unit having thereon a second grasping element for securing an opposite end of the graft tissue;
    the first grasping element being connected to the first unit by a tensioning device, the tensioning device comprising a base member and a sliding threaded shaft extending therethrough, the sliding threaded shaft being connected at one end to the first grasping element and at an opposite end to a grip;
    the tensioning device further including a spring mechanism on the threaded shaft;
    wherein when the spring mechanism is tensioned, rotation of the grip effects linear displacement of the sliding threaded shaft with respect to the first grasping element and base member.

* * * * *